United States Patent
Han et al.

(10) Patent No.: US 11,339,446 B2
(45) Date of Patent: May 24, 2022

(54) BIOMARKER FOR MEASUREMENT OF RESPONSE AND PROGNOSIS OF TRIPLE-NEGATIVE BREAST CANCER TO ANTICANCER AGENT

(71) Applicants: SEOUL NATIONAL UNIVERSITY R&DB FOUNDATION, Seoul (KR); INDUSTRY-ACADEMIC COOPERATION FOUNDATION OF SUNCHON NATIONAL UNIVERSITY, Suncheon-si (KR); SEOUL NATIONAL UNIVERSITY HOSPITAL, Seoul (KR)

(72) Inventors: Wonshik Han, Songpa-gu (KR); Dong-Young Noh, Yeongdeungpo-gu (KR); Han-Byoel Lee, Gangnam-gu (KR); Eun-Kyu Kim, Gangnam-gu (KR); Ae-Kyung Park, Seocho-gu (KR); Hyeong-Gon Moon, Nowon-gu (KR)

(73) Assignees: SEOUL NATIONAL UNIVERSITY R&DB FOUNDATION, Seoul (KR); INDUSTRY-ACADEMIC COOPERATION FOUNDATION OF SUNCHON NATIONAL UNIVERSITY, Suncheon-si (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 83 days.

(21) Appl. No.: 16/494,557

(22) PCT Filed: Mar. 8, 2018

(86) PCT No.: PCT/KR2018/002755
§ 371 (c)(1),
(2) Date: Sep. 16, 2019

(87) PCT Pub. No.: WO2018/169251
PCT Pub. Date: Sep. 20, 2018

(65) Prior Publication Data
US 2020/0087733 A1    Mar. 19, 2020

(30) Foreign Application Priority Data

Mar. 16, 2017 (KR) .................. 10-2017-0032929

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

FOREIGN PATENT DOCUMENTS

| KR | 10-2014-0105836 A | 9/2014 |
|---|---|---|
| KR | 10-1548830 B1 | 8/2015 |
| WO | 2016-196002 A1 | 12/2016 |
| WO | 2018-169251 A1 | 9/2018 |

OTHER PUBLICATIONS

GeneChip Gene 1.0 ST Array System Data Sheet, plus netaffx queries, Affymetrix. 2007. eight pates.*
Zhao et al. Journal of Clinical Oncology, vol. 19, No. 5 Mar. 1, 2001: pp. 1462-1467 (Year: 2001).*
Xie et al. BMC Cancer 2010, 10:591; 6 pages (Year: 2010) (Year: 2010).*
Parketal Clin Cancer Res 2009;15:5473-5477 (Year: 2009) (Year: 2009).*
VanGuilder et al. BioTechniques 44:619-626 (Year: 2008).*
Zheng, M. et al., "High GINS2 Transcript Level Predicts Poor Prognosis and Correlates with High Histological Grade and Endocrine Therapy Resistance through Mammary Cancer Stem Cells in Breast Cancer Patients", Breast Cancer Research and Treatment, 2014, vol. 148, pp. 423-436, See abstract; p. 429.
Loi, S., et al., "CD73 Promotes Anthracycline Resistance and Poor Prognosis in Triple Negative Breast Cancer", PNAS, 2013, vol. 110, No. 27, pp. 11091-11096, See the entire document.
International Search Report for PCT/KR2018/002755 dated Jul. 13, 2018, all pages.
Book Review, "*Methods in Molecular Biology*," vol. 1, *Proteins*. Edited by J.M. Walker, *Humana Press*, Clifton, N.J., 1984. 384 pp. , 1 page.
Chan-Hui, et al. "Applications of eTag™ assay platform to systems biology approaches in molecular oncology and toxicology studies," Clinical Immunology 111 (2004) 162-174, www.sciencedirect.com; 13 pages.
Colyer, et al., "Microchip-based capillary electrophoresis of human serum proteins," Journal of Chromatography a. 781 (1997) 271-276, 6 pages.
Petricoin III, et al., "Use of proteomic patterns in serum to identify ovarian cancer," The Lancet, vol. 359, Feb. 16, 2002, 6 pages.
Maggio, Edward T., "Enzyme-Immunoassay," CRC Press, 14 pages.
Han, et al., "Identification of Differentially Expressed Genes in Pancreatic Cancer Cells Using cDNA Microarray," Cancer Research 62, 2890-2896, May 15, 2002, 8 pages.
"*Methods in Molecular Biology*," Proteins, vol. 1, Edited by John M. Walker, 12 pages.
Montagne, et al., "Microparticle-Enhanced Nephelometric Immunoassay for Human C-Reactive Protein," Journal of Clinical Laboratory Analysis 6:24-29 (1992), 6 pages.

* cited by examiner

*Primary Examiner* — Juliet C Switzer
(74) *Attorney, Agent, or Firm* — Kilpatrick Townsend & Stockton LLP

(57) ABSTRACT

The present disclosure discloses a biomarker capable of predicting the therapeutic response to anticancer agents and prognosis of triple-negative breast cancer patients, and the use thereof. A biomarker according to the present disclosure allows the provision of optimized personal therapeutic methods through correct personalized treatment, contributing to the quality and prolongation of life of patients.

4 Claims, 15 Drawing Sheets

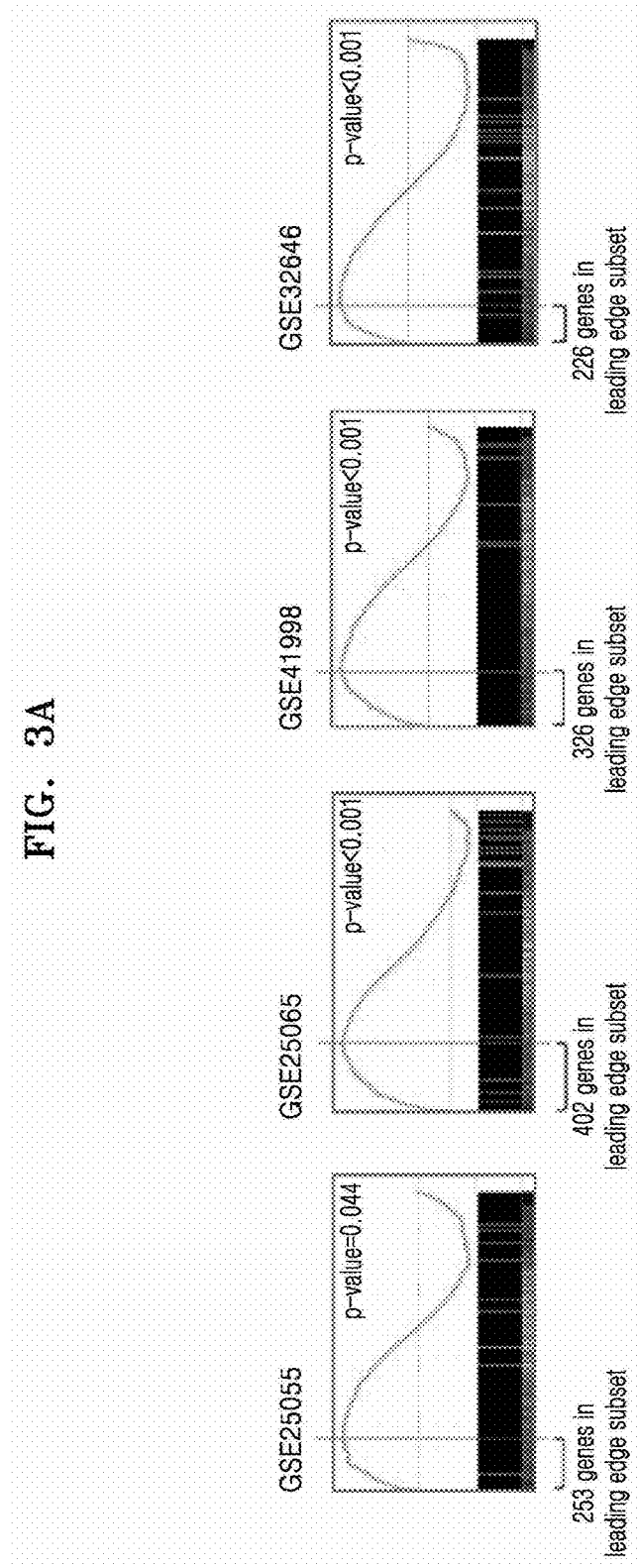

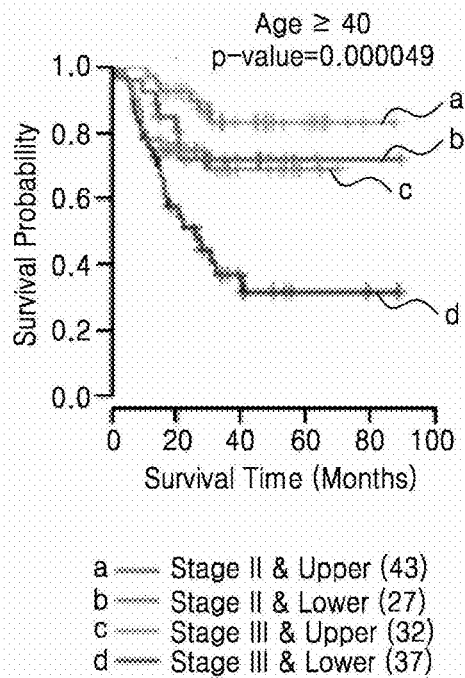
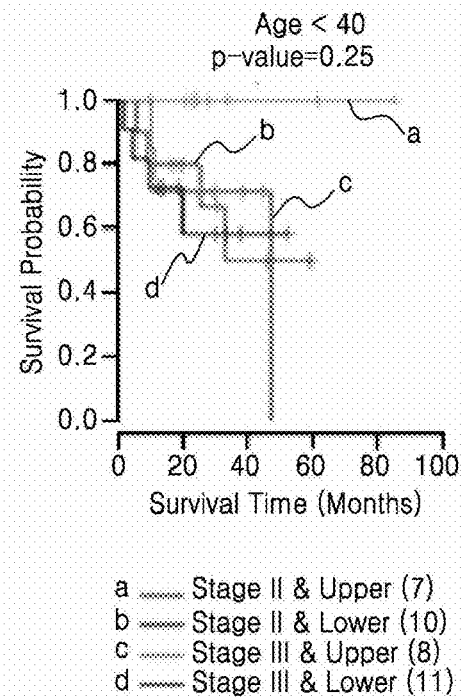

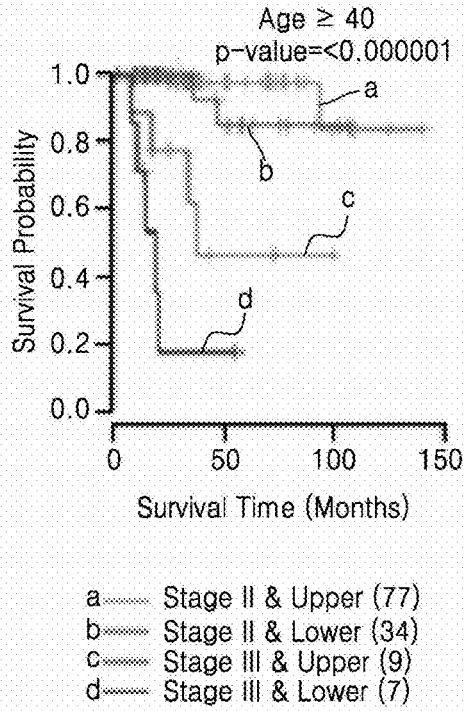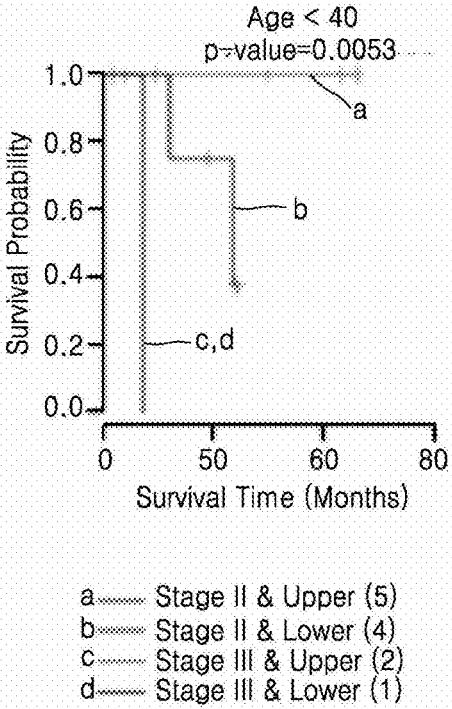

BIOMARKER FOR MEASUREMENT OF RESPONSE AND PROGNOSIS OF TRIPLE-NEGATIVE BREAST CANCER TO ANTICANCER AGENT

TECHNICAL FIELD

The present disclosure is in the technical field capable of predicting a therapeutic response or prognosis for an anticancer agent of breast cancer using a biomarker.

BACKGROUND ART

Triple-negative breast cancer tests negative for estrogen receptors (ER), progesterone receptors (PR), and HER-2 genes (HER2), and thus is concerned as an intractable breast cancer (ER-/PR-/HER2-). Triple-negative breast cancer is resistant to the existing hormone therapies and anti-HER2 treatments, and the frequency of metastasis and recurrence of such a cancer is high compared to other types of breast cancer.

As chemotherapeutic agents for triple-negative breast cancer, taxanes, anthracyclines, cyclophosphamides, and the like are used. When a response and prognosis of a patient for such anticancer agents can be determined before administration, through realization of personalized medicine and performance of targeted therapy, the survival and quality of life of patients suffering from unnecessary chemotherapy will be improved.

Therefore, there is a need for the development of a biomarker capable of predicting a therapeutic response (e.g., pathological complete response (pCR) vs. residual disease (RD)) of a patient to the administration of anticancer agents, or prognosis of a patient with triple-negative breast cancer using survival analysis based on variables, such as distant metastasis-free survival (DMFS), metastasis-related event-free survival, relapse-free survival (RFS), recurrence-free survival, or overall survival (OS), as dependent variables.

Korean Patent Publication No. 2012-0115390 relates to a method for predicting a response to therapy of triple-negative breast cancer, and discloses a biomarker of VEGFR2, c-KIT, HER1, or IGF-1R.

DESCRIPTION OF EMBODIMENTS

Technical Problem

The present disclosure is to provide a biomarker capable of predicting therapeutic response to anticancer agents and prognosis in a patient with triple-negative breast cancer, and performing a function as a target for the treatment of triple-negative breast cancer.

Solution to Problem

An aspect of the present disclosure provides use of the biomarker for predicting response to anticancer agents and prognosis in triple-negative breast cancer using one or more biomarkers of a first group, one or more biomarkers of a second group, or a combination of one or more biomarkers of each of the first and second groups.

The biomarker according to the present disclosure may include a polypeptide and/or a gene encoding the polypeptide.

Accordingly, there is provided use of the biomarker for predicting response to anticancer agents and prognosis in triple-negative breast cancer using one or more genes or polypeptides of the first group, one or more genes or polypeptides of the second group, or one or more genes or polypeptides of each of the first and second groups.

Alternatively, there is provided a polypeptide and/or a gene used for predicting response to anticancer agents and prognosis in triple-negative breast cancer.

The biomarker of the first group according to the present disclosure consists of CCAAT/enhancer-binding protein delta (CEBPD), matrix metalloproteinase-20 (MMP20), and wntless Wnt ligand secretion mediator (WLS), and the biomarker of the second group according to the present disclosure consists of anti-silencing function 1A histone chaperone (ASF1A), ALVEOLAR SOFT PART SARCOMA CHROMOSOME REGION (ASPSCR1), chromatin assembly factor 1 subunit B (CHAF1B), DNA methyltransferase 1 (DNMT1), GINS complex subunit 2 (GINS2), golgin subfamily A member 2B (GOLGA2P5), and spindle and kinetochore-associated protein 1 (SKA1), wherein the biomarkers of the two groups show opposite expression levels in terms of response to anticancer agents and prognosis Another aspect of the present disclosure also provides a method of determining a response to anticancer agents and prognosis in a patient with triple-negative breast cancer using the biomarker according to the present disclosure.

In the method according to an embodiment of the present disclosure, detection of the biomarker according to the present disclosure to determine response to anticancer agents and prognosis in a patient with triple-negative breast cancer includes: providing a biological sample derived from a target subject in need of the determination for the response to anticancer agents and prognosis measuring an expression level of one or more biomarkers of a first group and one or more biomarkers of a second group, at a nucleic acid level or a protein level from the biological sample, wherein the one or more biomarkers of the first group consist of CCAAT/enhancer-binding protein delta (CEBPD), matrix metalloproteinase-20 (MMP20), and wntless Wnt ligand secretion mediator (WLS), and the one or more biomarkers of the second group consist of anti-silencing function 1A histone chaperone (ASF1A), ALVEOLAR SOFT PART SARCOMA CHROMOSOME REGION (ASPSCR1), chromatin assembly factor 1 subunit B (CHAF1B), DNA methyltransferase 1 (DNMT1), GINS complex subunit 2 (GINS2), golgin subfamily A member 2B (GOLGA2P5), and spindle and kinetochore-associated protein 1 (SKA1); and associating the target subject with response to anticancer agents and prognosis by comparing the results of the measuring with those of a reference group.

In one embodiment, the associating includes determining that, when, compared to the reference group, an expression level of the one or more biomarkers of the first group increases and an expression level of the one or more biomarkers of the second group decreases, the target subject has poor response to anticancer agents and poor prognosis.

In one or more embodiments, the detection includes detecting of the one or more biomarkers of the first group and the one or more biomarkers of the second group, and the associating includes determining that, when, compared to the reference group, an expression level of the one or more biomarkers of the first group increases and an expression level of the one or more biomarkers of the second group decreases, the target subject has poor response to anticancer agents and poor prognosis.

Regarding the composition or the method according to the present disclosure, the anticancer agent includes a taxane-based anticancer agent including docetaxel, paclitaxel, or cabazitaxel, a vinca alkaloid anticancer agent including vincristine or vinblastine, anthracycline, 5-fluorouracil, or cyclophosphamide, but embodiments of the present disclosure are not limited thereto.

Regarding the composition or the method according to the present disclosure, the biological sample includes breast tissue, whole blood, lymph, serum, urine, plasma, circulating cancer cell, or nipple aspirate, but embodiments of the present disclosure are not limited thereto.

Advantageous Effects of Disclosure

A biomarker according to the present disclosure can accurately predict therapeutic response to anticancer agents and poor prognosis in triple-negative breast cancer using biomarkers of two groups with opposite expression patterns, so as to provide an individually optimized therapeutic methods through accurate personalized treatment, thereby contributing to the quality and prolongation of life of patients.

BRIEF DESCRIPTION OF DRAWINGS

FIG. 2A is a heat map showing the expressions of ER, PR, and HER2 in eight triple-negative TNBC cell lines, MCF7 cell line, which is positive to ER and PR, and HCC1954 cell line, which is HER-amplified. FIG. 2B is a heat map showing the degree of expression of candidate genes of the first gene markers, and shows a rank sum of intensity of chemo-resistance to docetaxel of triple-negative cell lines, wherein the candidate genes include 2,113 genes positively correlated with chemo-resistance to docetaxel (referred to as $1^{st}$ POS candidate genes) and 1,976 genes negatively correlated with chemo-resistance to docetaxel (referred to as $1^{st}$ NEG candidate genes) in eight triple-negative cell lines.

FIGS. 3A to 3D show a process of extracting gene markers for the second candidate genes correlated with chemo-resistance. The first candidate genes were used as pre-defined gene sets for gene set enrichment analysis (GSEA), and accordingly, genes included in leading edge subsets were extracted from four exploratory datasets. Then, genes commonly shown in the analysis of the four datasets were selected as "second candidate genes". FIG. 3A is a diagram showing the results of the GSEA analysis using the positively correlated gene sets (i.e., $1^{st}$ POS candidate genes). FIG. 3B is a diagram showing the results of the GSEA analysis using the negatively correlated gene sets (i.e., $1^{st}$ NEG candidate genes). FIG. 3C is a Venn diagram showing the results of FIG. 3A. FIG. 3D is a Venn diagram showing the results of FIG. 3B.

FIG. 4A is a heat map with relative expression levels (i.e., relative expression level value=(expression level of marker−minimum expression level of marker in tested group)/(maximum expression level of marker in tested group−minimum expression of maker in tested group)) in each patient of the ten finally selected genes, and up and down scores obtained by averaging the relative expression levels, wherein, in the heat map, genes are divided into a residual disease (RD) group and a pathological complete response (pCR) group. FIGS. 4B and 4C each show a scatter plot with x- and y-axes for up and down scores, respectively, obtained from expression of ten genes in the exploratory dataset, showing the survival analysis when the patients are divided into two or three groups based on a diagonal line (see Examples below). FIGS. 4D and 4E show the results of the survival analysis when the patients are divided in the validation dataset (i.e., five datasets with metastasis-related survival data) by the same method described above. FIGS. 4F and 4G show the results of the survival analysis when the patients are divided using other validation datasets, e.g., TCGA data, by the same method described above.

FIG. 5A is a heat map with up and down scores obtained by averaging the relative expression levels in each patient of the four genes (divided into a RD group and a pCR group). FIGS. 5B and 5C each show a scatter plot with x- and y-axes for up and down scores, respectively, obtained from four genes in the exploratory dataset, showing the survival analysis after the patients are divided into two or three groups based on a diagonal line (see Examples below). FIGS. 5D and 5E show the results of the survival analysis after the patients are divided in the verification dataset (i.e., five datasets with metastasis-related survival data) by the same method described above. FIGS. 5F and 5G show the results of the survival analysis when the patients are divided using other verification datasets, e.g., TCGA data, by the same method described above.

FIGS. 6A to 6D show the results of the survival analysis performed after dividing patients by age at diagnosis and stage at the time of diagnosing patients with breast cancer in terms of up and down scores that are obtained from four genes. FIGS. 6A and 6B show the results obtained from the exploratory dataset, and FIGS. 6C and 6D show the results obtained from the TCGA datasets.

MODE OF DISCLOSURE

Figure 1:
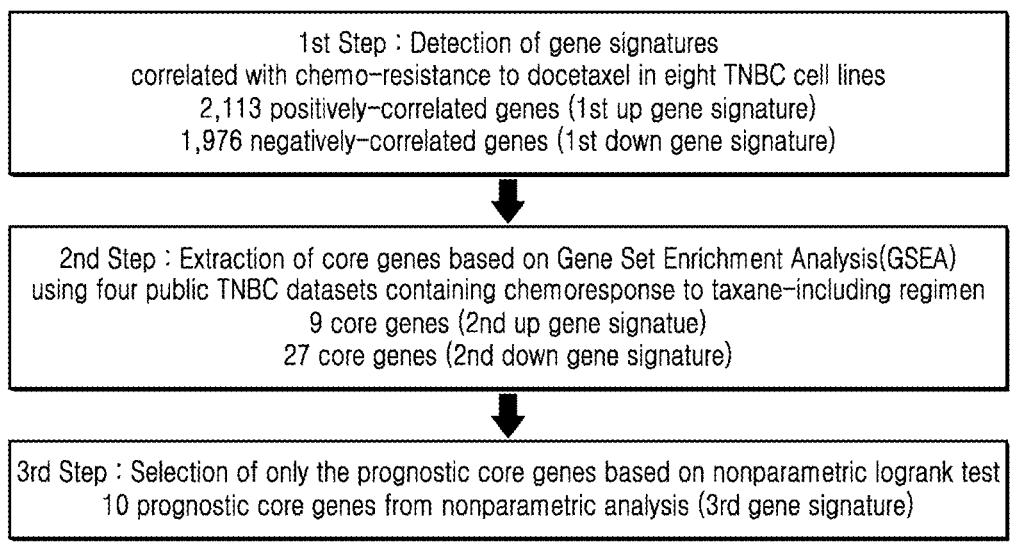
FIG. 1 schematically illustrates three steps used to identify core genes correlated with a therapeutic response and prognosis.

The present disclosure is based on the identification of biomarkers that are differentially expressed in connection with chemoresponse and survival rates in a patient with triple-negative breast cancer.

In particular, the present disclosure enables accurate prediction of resistance (or response) to an anticancer agent and prognosis in a patient with triple-negative breast cancer by discovering a biomarker of a first group and a biomarker of a second group with different expression patterns in connection with response to an anticancer agent and survival rates.

In this regard, the present disclosure provides: CCAAT/enhancer-binding protein delta (CEBPD), matrix metalloproteinase-20 (MMP20), or wntless Wnt ligand secretion mediator (WLS), as a biomarker of a first group that can predict therapeutic response to an anticancer agent and prognosis of triple-negative breast cancer; and anti-silencing function 1A histone chaperone (ASF1A), ALVEOLAR SOFT PART SARCOMA CHROMOSOME REGION (ASPSCR1), chromatin assembly factor 1 subunit B (CHAF1B), DNA methyltransferase 1 (DNMT1), GINS complex subunit 2 (GINS2), golgin subfamily A member 2B (GOLGA2P5), and spindle and kinetochore-associated protein 1 (SKA1), as a biomarker of a second group.

The biomarkers of the first group and the second group according to the present disclosure have different expression patterns. That is, when the expression of CEBPD, MMP20, or WLS belonging to the first group increases, such a biomarker was found to have poor response to an anticancer agent and prognosis, whereas when the expression of ASF1A, ASPSCR1, CHAF1B, DNMT1, GINS2, GOLGA2P5, or SKA1 belonging to the second group decreases, such a biomarker was found to have poor response to an anticancer agent and prognosis.

Also, alternatively, when the expression of CEBPD, MMP20, or WLS decreases, such a biomarker was found to have excellent or good response to an anticancer agent and prognosis, whereas when the expression of ASF1A, ASPSCR1, CHAF1B, DNMT1, GINS2, GOLGA2P5, or SKA1 decreases, such a biomarker was found to have good response to an anticancer agent and prognosis. No response with an anticancer agent indicates resistance to the anticancer agent, whereas response with an anticancer agent indicates possible treatment of cancer using an anticancer agent. The response or resistance to the anticancer agent may be determined depending on the context.

An aspect of the present disclosure provides a composition for determining chemoresponse or prognosis for the treatment of triple-negative breast cancer using an anticancer agent including a detection reagent or a detection material of one or more biomarkers of the first group and/or one or more biomarkers of the second group.

A patient allowing use of the biomarkers according to the present disclosure is the one diagnosed with, especially, triple-negative breast cancer. Triple-negative breast cancer (TNBC) is cancer without estrogen receptors, progesteron receptors, or epidemal growth factor (e.g., HER2) rexeptors, and is denoted as ER-/PR-/HER2-. Diagnosis of TNBC may be determined using biopsy tissue according to known methods such as immunohistostaining assay.

In the case of TNBC, since hormone therapy and HER2 targeted therapy are not effective, chemotherapy is the only treatment for systemic therapy in a patient. In chemotherapy of breast cancer, combination chemotherapy of anthracyclines, such as doxorubicin-cyclophosphamide (AC), or combination chemotherapy of AC-fluorouracil, AC-taxol (paclitaxel), or AC-taxotere (docetaxel). Here, the use of taxane-based drugs, such as paclitaxel and docetaxel, together is known to be more effective.

However, some of TNBC patients show resistance to chemotherapy, and such resistance will directly affect the prognosis of the patients. The progression of taxane-based chemotherapy to patients with breast cancer who show resistance results in progression of painful treatment that does nothing to improve the treatment effects.

Therefore, when the response in TNBC patients to chemotherapy using, for example, taxane-based drugs, is predictable, to patients showing resistance, unnecessary chemotherapy may be omitted or chemotherapy using other drugs may be considered, resulting in many advantages such as improvement of the life quality of patients, increase of survival rates, and reduction in costs.

In the present disclosure, the markers disclosed herein were used for analyzing samples of patients treated with various anticancer agents or by combinational chemotherapy as described in Examples herein, and as a result, significant results on the prediction of chemoresponse and prognosis were obtained.

In one embodiment, examples of the taxane-based anticancer agent include docetaxel, paclitaxel, and cabazitaxel, but embodiments of the present disclosure are not limited thereto.

In one or more embodiments, vinca alkaloids (e.g., vincristine and vinblastine) and the like, which have a similar mechanism with the taxane-based anticancer agent (e.g., spindle poison or microtubule inhibitor mechanism) may be also used. In addition, in screening of markers as described in Examples herein, chemotherapy used in the second and third stages is associated with a combination of not only patients administered with taxane, but also patients administered with cyclophosphamide, anthracycline (e.g., epirubicin or doxorubicin), or 5-fluorouracil, and in this regard, the marker according to the present disclosure may be used as a marker for resistance to a wide range of anticancer agents including various anticancer agents (e.g., axane-anthracycline (GSE25055 and GSE25065, collectively designated GSE25066), paclitaxel followed by 5-fluorouracil/epirubicin/cyclophosphamide (GSE32646), and doxorubicin/cyclophosphamide followed by paclitaxel (GSE41998)).

In the present disclosure, the biomarker may include a protein or a nucleic acid encoding the protein, or a peptide or a metabolite thereof. In one embodiment, the biomarker according to the present disclosure may include a protein, a peptide, or a nucleic acid encoding the protein or the peptide.

The biomarker according to the present disclosure may be detected in a biological sample. Such a biological sample may include breast tissue, whole blood, lymph, serum, urine, plasma, circulating cancer cell, and/or nipple aspirate, but embodiments of the present disclosure are not limited thereto.

In the present disclosure, the poor prognosis refers to a case where distance metastasis occurs within 5 years after diagnosis, and the excellent or good prognosis refers to a case where no metastasis occurs in other organs in 5 years after diagnosis. However, embodiments of the present disclosure are not limited thereto.

In one embodiment, the determination of the prognosis may be achieved using metastasis-related survival outcome, for example, distant relapse-free survival (DRFS), or distant metastasis-free survival (DMFS) described in Examples herein, metastasis-free survival (MFS), relapse-free survival, event-free survival, or overall survival.

The increase or decrease in survival rates of a patient may be determined using methods such as Kaplan-Meier Meter survival curve, logrank test, Cox regression.

Through quantitative or qualitative analysis, the marker according to the present disclosure may be detected depending on the presence of a nucleic acid (particularly, mRNA) and/or a protein, and/or detected at the level of expression of the nucleic acid or the protein itself, changes in expression levels, and differences in the expression levels.

In one embodiment, the marker according to the present disclosure may be quantitatively analyzed.

The detection of the biomarker according to the present disclosure may be based on functional features and/or antigenic features of the biomarker. The marker according to the present disclosure may be detected by detecting activity or function of the marker, or by using a substance that specifically interacts at a nucleic acid (particularly, mRNA) level and/or a protein level.

In this regard, a detection reagent according to the present disclosure may be the one that can detect the marker according to the present disclosure in a quantitative or qualitative analysis in various ways at a protein level or a nucleic acid level.

For the quantitative and qualitative analysis of the marker according to the present disclosure, various methods of qualitatively or quantitatively detecting known nucleic acids and proteins may be used. Protein sequences and gene sequences of the biomarker according to the present disclosure are provided in Table 1 below.

TABLE 1

| Symbol of marker gene of present disclosure | Gene sequence DB number | Protein sequence DB number |
| --- | --- | --- |
| CEBPD | NM_005195.3 | NP_005186.2 |
| MMP20 | NM_004771.3 | NP_004762.2 |
| WLS | NM_001002292.3 | NP_001002292.3 |
| ASF1A | NM_014034.2 | NP_054753.1 |
| ASPSCR1 | NM_001251888.1 | NP_001238817.1 |
| CHAF1B | NM_055441.2 | NP_005432.1 |
| DNMT1 | NM_001130823.2 | NP_001124295. |
| GINS2 | NM_016095.2 | NP_057179.1 |
| GOLGA2P5 | MN_017600.1 | NP_060070.1 |
| SKA1 | NM_001039535.2 | NP_001034624.1 |

For qualitative or quantitative detection at the protein level, for example, Western blotting, enzyme linked immuno sorbent assay (ELISA), radio immuno assay (RIA), immunodiffusion, immunoelectrophoresis, tissue immunostaining, immunoprecipitation assay, complement fixation assay, detection using binding with labeled antibodies in solution/suspension or using a flow cytometer, or methods using a mass spectrometer or a protein array such as antibody may be used.

Alternatively, for qualitative or quantitative detection at the nucleic acid level, methods using nucleic acid transcription and amplification system, eTag system, system based on labeled beads, or array system such as nucleic acid array may be used.

Such methods are known, and for example, may be referred by chip-based capillary electrophoresis: Colyer et al. 1997. J Chromatogr A. 781(1-2):271-6; mass spectroscopy: Petricoin et al. 2002. Lancet 359: 572-77; eTag systems: Chan-Hui et al. 2004. Clinical Immunology 111: 162-174; microparticle-enhanced nephelometric immunoassay: Montagne et al. 1992. Eur J Clin Chem Clin Biochem. 30:217-22.

In one embodiment, a sandwich immunoassay, such as ELISA or RIA, may be used. In the method, a biological sample may be provided to a first antibody bound to beads, membranes, slides, or microtiterplates made of a solid substrate, for example, glass, plastic (e.g., polystyrene), polysaccharide, nylon, or nitrocellulose. Then, proteins may be detected qualitatively or quantitatively by labeling with a labeling material capable of direct or indirect detection, for example, a radioactive material, such as $^3$H or $^{125}$I, a fluorescent material, a chemiluminescent material, hepten, biotin, digoxygenin, or the like, or through binding of conjugated antibodies with an enzyme, such as horseradish peroxidase, which can be colored or emitted through an action with a substrate, alkaline phosphatase, alkaline phosphatase, and malate dehydrogenase.

In one or more embodiments, immunoelectrophoresis (IE), such as an Ouchterlony plate, which can simply detect a marker through an antigen-antibody binding, Western blotting, Crossed IE, Rocket IE, Fused Rocket IE, or Affinity IE, may be used. The immunoassay or immunostaining method was described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984, or the like. By analyzing the intensity of final signals by the immunoassay process described above, i.e., by performing a signal comparison with a normal sample, occurrence of a disease may be diagnosed.

Reagents or materials used in such methods are known in the art, and for example, antibodies, substrates, nucleic acids, or peptide aptamers that specifically bind to the marker, or receptors, ligands, or supplementary factors that specifically interact with the marker may be used. The reagents or materials that specifically interact with or bind to the marker according to the present disclosure may be used with chips or nanoparticles.

The marker according to the present disclosure may be detected quantitatively and/or qualitatively using a variety of methods known at the nucleic acid level, particularly, at the mRNA level.

For qualitative or quantitative detection at the nucleic acid level, for example, reverse-transcription polymerase chain reaction (RT-PCR)/polymerase chain reaction for detection at the mRNA level or detection of expression levels or patterns, competitive RT-PCR, real-time RT-PCR, nuclease protection assay (NPA), such as RNase, S1 nuclease analysis, in-situ hybridization, DNA microarray or chip, nanostring, next-generation sequencing (NGS), or northern blotting, may be used. Such assays are known in the art, and may be also performed using commercially available kits. Also, one of ordinary skill in the art will be able to select appropriate assay for the practice of the present disclosure. For example, Northern blotting has advantages of identifying the size of transcripts present in cells and using various probes. NPA is useful for the analysis of multiple markers, in-situ hybridization is useful for locating transcripts, such as mRNA, in cells or tissues, and RT-PCR is useful for detecting small amounts of samples. In addition, a binding agent that specifically binds to a nucleic acid, such as mRNA or cRNA, derived from a gene encoding a protein of the biomarker according to the present disclosure, or an array including the binding agent may be used.

Reagents or substances used in the detection of the biomarker at the nucleic acid level are known in the art. For example, a detection reagent used in a method of measuring the presence of mRNA and an amount thereof by RT-PCR may include, for example, a probe and/or a primer pair specific to mRNA of the biomarker according to the present disclosure. The "primer" or "probe" refers to a nucleic acid sequence having a free 3' hydroxyl group capable of binding complementarily to a template and allowing a reverse transcriptase of DNA polymerase to initiate replication of the template. The detection reagent used herein may be labeled with a colorant, luminescent, or fluorescent substance as described above for signal detection. In one embodiment, Northern blotting or RT-PCR may be used for mRNA detection. In the latter case, RNA (specifically, mRNA) of a sample is separated, cDNA is synthesized therefrom, and then, a specific gene in the sample is detected by using a specific primer or a combination of primers and probes, thereby determining the presence/absence of the specific gene or expression levels of the specific gene. Such a method is described in, for example, ((Han, H. et al, 2002. Cancer Res. 62: 2890-6).

The biomarker used herein may be used for predicting therapeutic response to the anticancer agent and prognosis in a TNBC patient.

In one embodiment, the method disclosed herein includes: to provide information needed to determine response to an anticancer agent and prognosis in a TNBC patient, providing a biological sample derived from a target subject in need of the determination for chemoresponse or prognosis; measuring an expression level of a biomarker at a nucleic acid or protein level from the sample, the biomarker including one or more biomarkers of the first group consisting of CEBPD, MMP20, and WLS, or one or more biomarkers of the second group consisting of ASF1A, ASPSCR1, CJAF1B, DNMT1, GINS2, GOLGA2P5, and SKA1, or one or more biomarkers of each of the first group and the second group; and associating the target subject with response to an anticancer agent and prognosis by comparing the results obtained in the measuring with those of a reference group.

In one embodiment, the measuring further includes the steps of: determining a relative expression level of each of the biomarkers of the first group and the second group based on the measured expression level; calculating an up score by averaging the relative expression level of the one or more biomarkers of the first group; and calculating a down score by averaging the relative expression level of the one or more biomarkers of the second group. The expression level of each biomarker according to the present disclosure may be determined by, for example, quantitative RT-PCR or Western blotting, and a value obtained therefrom, i.e., an expression level, may be converted into a relative expression level. The relative expression level may be obtained from the formula: relative value=(expression level of marker−minimum expression level of marker in tested group (Min))/(maximum expression level of marker in tested group (Max)−Min).

In one embodiment, in the associating, the results of the reference group are shown in a scatter plot in which an x-axis represents the up score of the biomarker of the first group and a y-axis represents the down scores of the biomarker of the second group, wherein the up and down scores are determined from many TNBC patients receiving chemotherapy. The scatter plot includes a first diagonal line passing through a point where the median value of the up score is indicated as x and the median value of the down score is indicated as y, and having a slope determined by a value with a denominator and a numerator, wherein the denominator is obtained by subtracting a minimum value from a maximum value of the up score and the numerator is obtained by subtracting a minimum value from a maximum value of the down score. The calculation of the median and the diagonal line with a specific slope based on the median and the numerator/denominator value may be obtained by known methods in the art.

As shown in FIG. 4, when the up and down scores determined in the target subject are plotted into the scatter plot, and the point belongs to a region above the diagonal line, the target subject is determined to have good response to the anticancer agent and good prognosis. Meanwhile, when the point belongs to a region below the diagonal line, the target subject is determined to have poor response to the anticancer agent and poor prognosis.

In one embodiment, the scatter plot in the associating may further include a second diagonal line having the same slope as the first diagonal line but a different y-intercept and dividing the scatter plot into 25%, 50%, and 25%. In this case, as shown in FIG. 5, the prognosis is determined to be poorer as the scores are located above the first diagonal line, between the first and second diagonal lines, and below the second diagonal line.

The patient in the reference group is a TNBC patient who has received chemotherapy, i.e., a patient with information on the response to the anticancer agent. As a result of associating the clinical information (i.e., response to an anticancer agent and prognosis) about each patient with the scatter plot, it is confirmed that the response to an anticancer agent and prognosis were reproducibly predictable based on the diagonal line determined as described above.

Accordingly, in one embodiment, when the up and down scores determined in the target subject are plotted into the scatter plot in the associating, and the point belongs to a region above the diagonal line, the target subject is determined to have good response to the anticancer agent and good prognosis. Meanwhile, when the point belongs to a region below the diagonal line, the target subject is determined to have poor response to the anticancer agent and poor prognosis.

In one or more embodiments, in the associating, when the expression of the one or more biomarkers of the first group increases compared to the reference group, and/or when the expression of the one or more biomarkers of the second group decreases compared to the reference group, the target subject is determined to have poor response to the anticancer agent and poor prognosis. In this case, the increase or decrease of the expression level of the biomarker according to the present disclosure may be determined in comparison with the reference group. For example, in one embodiment, the reference group may include database of gene expression levels measured in samples of many TNBC patients. In one or more embodiments, the reference group may include database of gene expression levels of TNBC patients obtained from a published database. That is, based on the gene expression information measured from samples of TNBC patients secured from the database published by the National Center for Biotechnology Information (NCBI), the Cancer Genome Atlas Cancer Genome (TCGA), the Gene Expression Omnibus (GEO), the ArrayExpress, the Short Read Archive (SRA), or the like, the median expression level of each gene expression level may be determined and referred to as the database of the reference group. For example, methods used in Examples herein and FIGS. 4B to 4G or FIGS. 5B to 5G may be referred. That is, for each gene, the ranking of gene expression levels is determined from a number of TNBC patient samples. Then, the maximum expression level is defined as a maximum value, the minimum expression level is defined as a minimum value, and an expression level at the 50% position is defined as a median expression level. On this basis, when the gene expression level is smaller than the median expression level, the expression level is considered to be decreased, and when the gene expression level is greater than the median expression level, the expression level is considered to be increased.

Figure 4A:
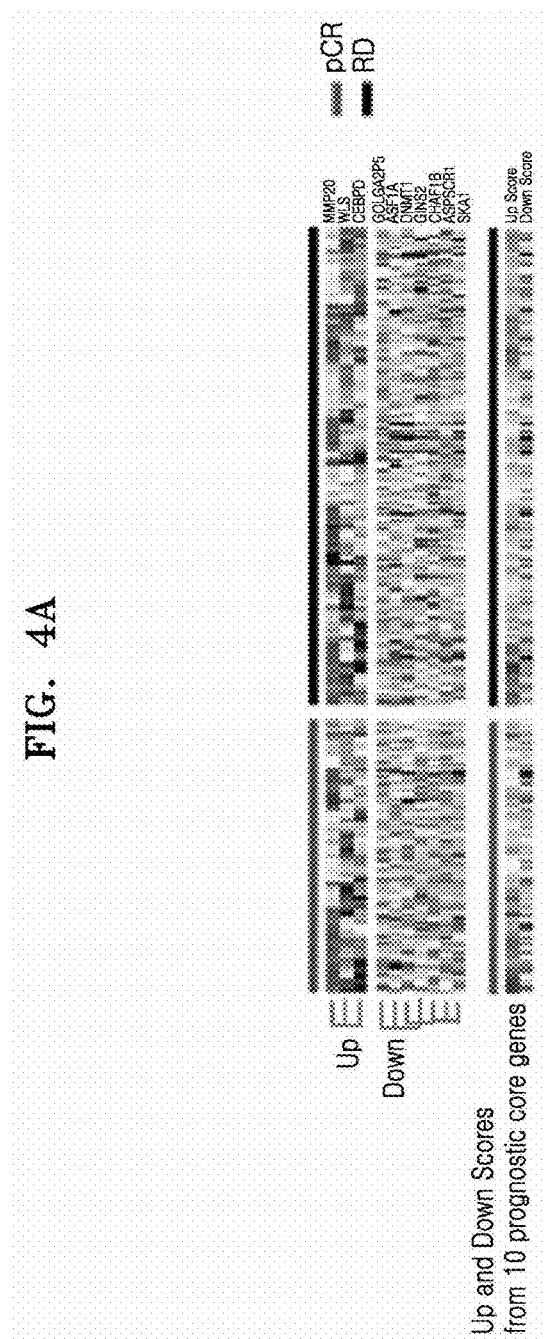
FIGS. 4A to 4G show the results of verifying the prognostic predictive ability of ten third gene markers (referred to as ten prognostic core genes) that are finally selected from the second candidate genes by the logrank test.
Figure 4B:
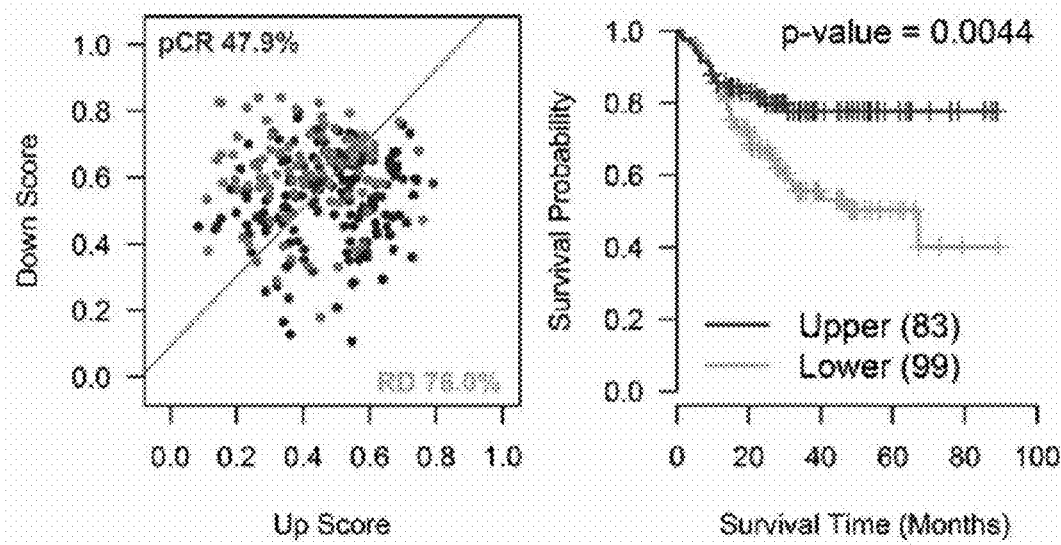
Figure 4C:
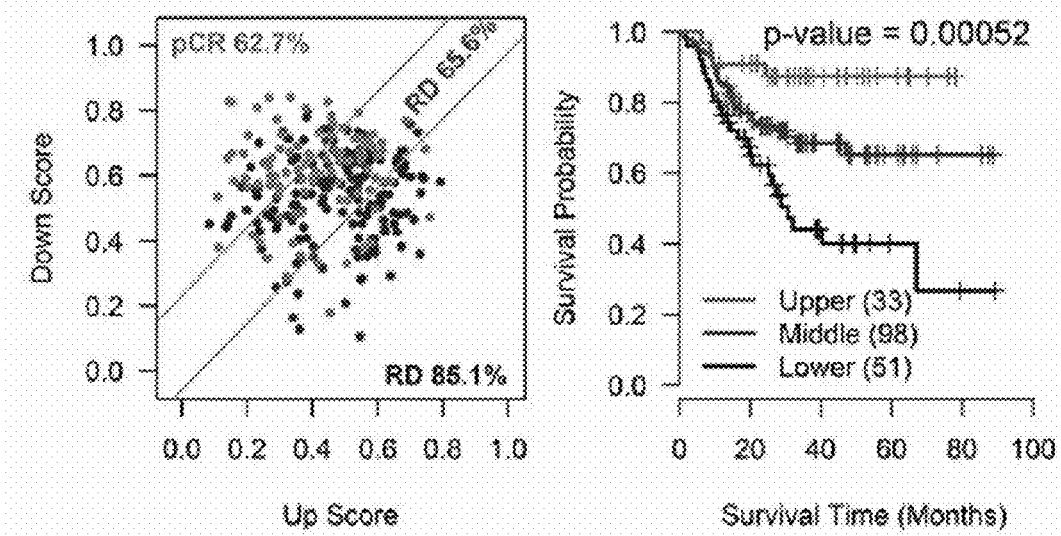
Figure 4D:
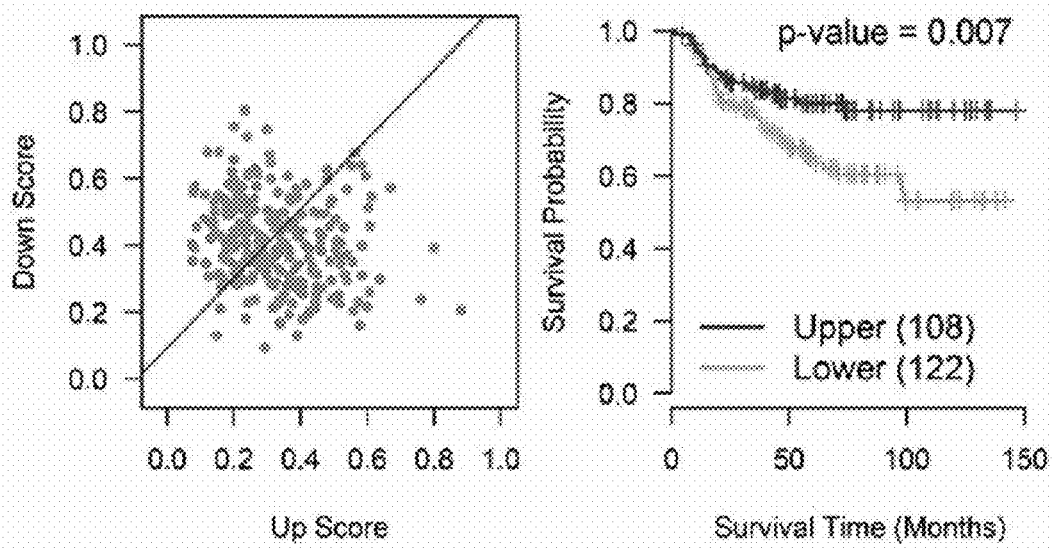
Figure 4E:
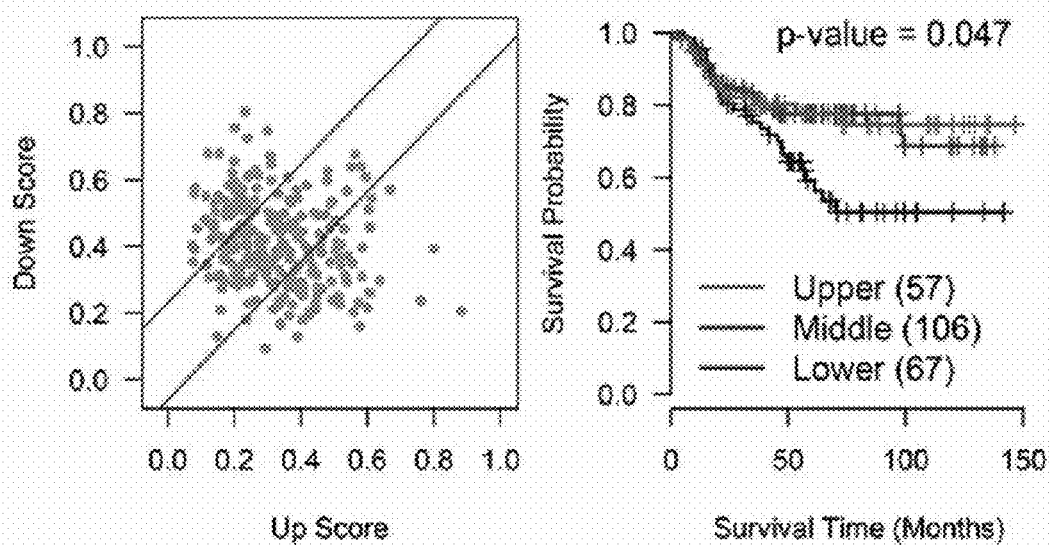
Figure 4F:
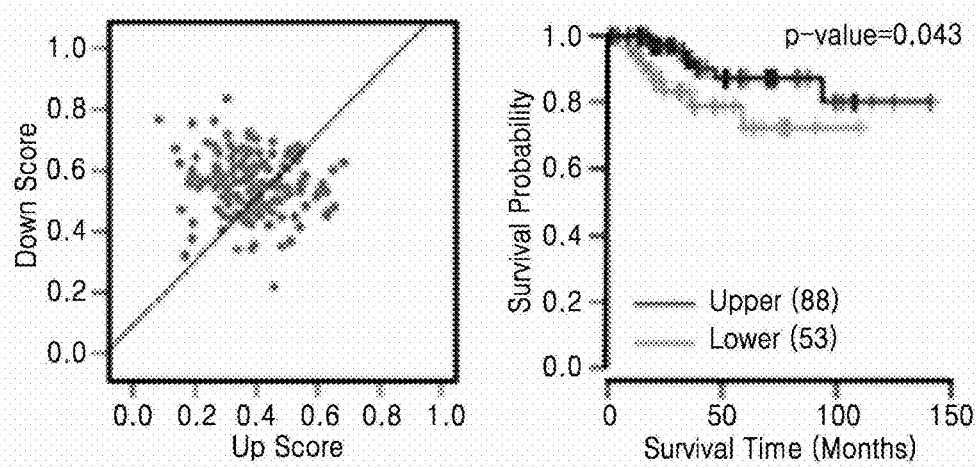
Figure 4G:
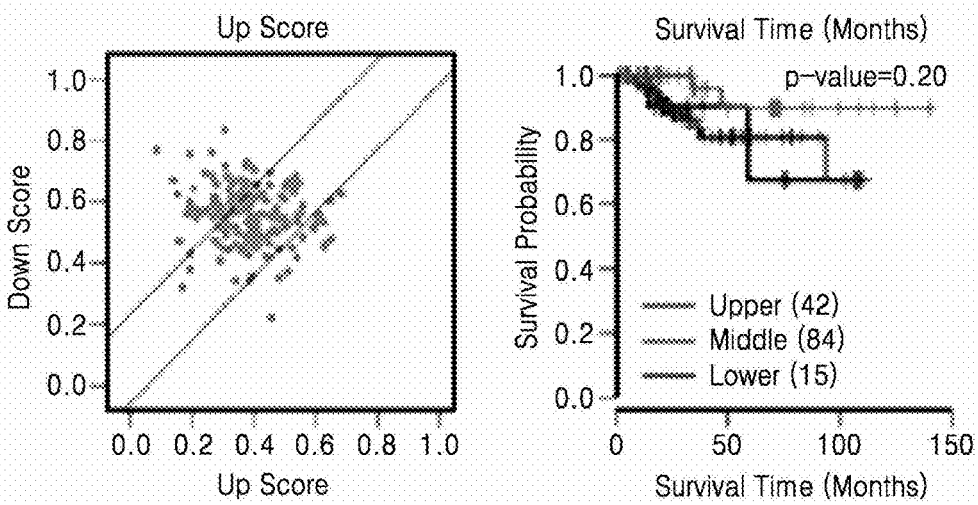

In addition, based on the expression level and referring to FIGS. 4B and 4C, as a result of the comparison with the reference group, determinations may be made depending on the combination of expression of markers of the first group and the second group: when the expression level of the biomarker of the first group increases and the expression level of the biomarker of the second group decreases, the target subject is determined to have the poorest prognosis; a case where the expression level of the biomarker of the first group decreases and the expression level of the biomarker of the second group increases, the target subject is determined to have good prognosis; and cases where the expression level of the biomarker of the first group increases and the expression level of the biomarker of the second group also increases, the expression level of the biomarker of the first group decreases and the expression level of the biomarker of the second group also decreases, and the expression levels of the both biomarkers of the first and second groups are median or mean values or similar therewith, the target subject is determined to have neither good nor poor prognosis. One of ordinary skill in the art will be able to easily determine the median prognosis by determining ranges similar to the median and mean values.

In the results of the reference group, 10 or more, 20 or more, 30 or more, 40 or more, 50 or more, and 50 or more of the TNBC tissue samples may be used. As the number of the samples increases, the reliability of the reference group also increases, but one of ordinary skill in the art will be able to easily determine an appropriate number of the samples. The median value may be determined using known statistical analysis, such as Z-score or the like.

The target subject according to the present disclosure refers to a TNBC patient, especially, a person in need of chemotherapy. The anticancer agent used herein is as described above.

The detection method of the biological samples and the markers used in the method according to the present disclosure is as described above. In the method according to the present disclosure, the sample is not particularly limited as long as it can detect the differential expression of the marker according to the present disclosure, and for example, breast tissue, whole blood, lymph, serum, urine, plasma, circulating cancer cell, and/or nipple aspirate may be used.

Hereinafter, Examples are provided to help understanding of the present disclosure. However, the following Examples are merely provided to more easily understand the present disclosure, and the present disclosure is not limited to the following Examples.

EXAMPLES

Protocols

Cytotoxicity Experiments and Microarray Analysis of 8 TNBC Cell Lines

MDA-MB-231, DU4475, MDA-MB-436, and MDA-MB-157 cell lines were purchased from the ATCC. MDA-MB-468, HCC1937, HS578T, and HCC38 cell lines were obtained from the Korea Cell Bank. MDA-MB-157 cell line was cultured in a Leibovitz's L15 culture medium supplemented with 10% fetal bovine serum. The MDA-MB-436 cell line was cultured in a Leibovitz's L15 culture medium supplemented with 10% fetal bovine serum and 0.026 units/ml units insulin. The MDA-MB-231 cell line, the MDA-MB-468 cell line, and the HS578T cell line were each cultured in a DMEM culture medium supplemented with 10% fetal bovine serum in 5% $CO_2$. The remaining cell lines were each cultured in a RPMI-1640 culture medium supplemented with 10% fetal bovine serum in 5% $CO_2$.

In the present disclosure, docetaxel was used to find genes related to resistance to taxane-based neoadjuvant chemotherapy (NAC). Docetaxel was purchased at Sigma-Aldrich, and then, dissolved according to the instructions of the manufacturer. The cell lines were collected using trypsin treatment, counted with a hemocytometer, and plated for 14 hours at a density of 3,000 cells/well in a 96-well plate. Afterwards, the solvent was replaced with docetaxel at different concentrations (e.g., 0 nM, 0.01 nM, 0.1 nM, 1 nM, 10 nM, and 100 nM), 48 hours after exposure to docetaxel, cell viability experiments were performed using the CellTiter-Glo Luminescent Cell Viability Assay according to the protocol of the manufacture. The CellTiter-Glo Luminescent Cell Viability Assay is a method of determining the number of cells present in a culture medium depending on the amount of ATP in a culture medium. In summary, the same amount of 100 μl of CellTiter-Glo assay reagents were added to each well, incubated for 10 minutes at room temperature, and then, measured according to the luminometry. The experiment was repeated twice, and the 50% inhibitory concentration of each cell line was measured by non-linear regression analysis.

Total RNAs for the microarray chip were extracted and amplified from each cell line using the Qiagen RNeasy Mini kit, and then, labeled according to the Affymetrix GeneChip Whole Transcript Sense Target Labeling protocol. Then, resulting cDNAs were hybridized to Affymetrix Human Gene 1.0 ST arrays. The scanned gene expression values were pre-treated according to the Robust Multi-array Average (RMA) method, and converted into $log_2$.

Exploring First Candidate Genes Related to Taxane Resistance

Two criteria were used to find genes related to docetaxel resistance in the TNBC cell lines: (1) the degree of changes in gene expression in 8 cell lines (|ΔEx|) (i.e., a difference between a maximum expression value and a minimum expression value), i.e., the degree of changes in gene expression in 8 cell lines ((|ΔEx|) is greater than 1; (2) the absolute value (|r|) of the correlation coefficient between the gene expression levels and the rank sum of genes showing resistance to the anticancer agent is greater than 0.5. That is, when each cell line is ranked in order of resistance to docetaxel, the rank sum (i.e., the sum of two rank values determined by the order to survival rates after treatment with docetaxel at two concentrations (i.e., 50 nM and 100 nM)) is calculated, and at least one of two absolute values (|r|) is greater than 0.5 after calculating correlation coefficient of Pearsons or Spearmans between the sum and the gene expression, the gene is considered to be related to docetaxel resistance. The genes obtained from the analysis of 8 TNBC cell lines in the manner were called "first genes related to taxene resistance".

Specification of Gene Marker Ranges for Taxane Resistance Using Public Datasets Including Responses to Neoadjuvant Chemotherapy (NAC) with Taxane To reduce the number of "candidate first genes related to taxane resistance", the following public data were used from the Gene Expression Omnibus (GEO). That is, 4 data (i.e., GSE25055, GSE25065, GSE32646, and GSE41998) including information on the response to the NAC (i.e., pathological complete response (pCR) vs. residual disease (RD)) and the gene expression (i.e., microarray) were collected. The chemotherapy used in patients of each dataset is as follows: taxane-anthracycline (GSE25055 and GSE25065, GSE25066 of two combinations), 5-fluorouracil/epirubicin/cyclophosphamide followed by paclitaxel (GSE32646), paclitaxel followed by doxorubicin/cyclophosphamide (GSE41998).

Each microarray raw data was downloaded and pre-treated using the RMA algorithm. In the case of GSE25055 and GSE25065, the data that were already pre-treated and normalized were downloaded from the GEO. To classify data as TNBC data and non-TNBC data, TNBC data were extracted by using cut-off points where two normal distribution curves meet as the distributions of expression levels of ER, PR, and HER2 are set to two normal distributions with, respectively. The TNBC datasets (also known as exploratory datasets) finally obtained from 4 data sets consist of the chemoresponse information (i.e., (pCR vs RD) of chemotherapy from 265 patients, survival data (i.e., distant relapse-free survival (DRFS)) from 182 patients, and microarray data ((119 patients from GSE25055, 63 patients from GSE25065, 64 patients from GSE41998, and 25 patients from GSE32646) from 271 patients. The Gene Set Enrichment Analysis (GSEA) was performed on each of the four exploratory datasets. That is, genes were ranked by the expression difference (i.e., fold change (log 2)) between RD and pCR groups for each gene, and the GSEA method was applied using "candidate first genes related to taxane resistance" (two gene sets divided in positive and negative up and down, respectively) as predefined gene sets (using the GseaPreranked program of the GSEA). Finally, the core genes of the leading-edge subset generated from the GSEA results were extracted from each dataset analysis result, and the core genes commonly found in the 4 data analysis were designated as "second candidate genes related to anticancer agent resistance".

Selection of Core Genes Related to Prognosis Based on Survival Analysis Results Using Exploratory Dataset Next, as a third step, genes related to prognosis were selected from second candidate genes related to response to the anticancer agent. For the selection, the nonparametric logrank tests were performed using the GSE25066 (i.e., GSE25055 and GSE25065) dataset including TNBC patient information, i.e., DRFS information. That is, for each gene of the "second candidate genes related to resistance to the anticancer agent", 3 cut-off points (i.e., 0.25, 0.5, and 0.75 quantile) were used to divide patients into a high-expression group and a low-expression group, and the survival analysis was performed using logrank tests. 3 comparisons were made as logrank tests between the distributions of the two groups. When any of these three analyzes was considered statistically significant (p-value<0.05), the gene was called a "third core gene related to prognosis". When Cox regression was applied and the statistical significance (p-value<0.05) was obtained, the gene was called a "third core gene related to prognosis".

Validation of Third Core Gene Based on Survival Analysis Using Exploratory Dataset For the validation analysis, the following data were used. A total of 6 breast cancer datasets were collected as follows: the Cancer Genome Atlas (TCGA) dataset including overall survival outcome, 13 GEO datasets (GSE16446, GSE19615, GSE20685, GSE22219, GSE2603) including metastasis-related event-free survival outcome, such as distant relapse-free survival (DRFS DRFS), distant metastasis-free survival) DMFS), or metastasis-free survival (MFS). The preprocessing of the raw data and the selection process of the TNBC samples were performed as described above.

First, to examine the effect of the third core genes related to prognosis (i.e., markers according to the present disclosure) on the prognosis in the TNBC patients undergoing chemotherapy, TNBC data (GSE16446, GSE19615, GSE20685, GSE22219, GSE2603) of 246 patients undergoing chemotherapy, i.e., 5 datasets, were used. Among these data, the survival outcome data (i.e., DRFS, DMFS, or MFS) of the 230 patients were used. Specific information on chemotherapy in these 5 datasets is as follows: neoadjuvant chemotherapy (GSE16446) or adjuvant chemotherapy (GSE19615, GSE20685, GSE22219, and GSE2603), anthracycline (GSE16446), doxorubicin and cyclophosphamide followed by taxol (AC-taxol), ACx4, or cyclophosphamide/doxorubicin/5-fluorouracil (CAF) (GSE19615), CAF, cyclophosphamide/methotrexate/5-fluorouracil (CMF), or others (GSE20685), CMF (GSE22219), and adjuvant chemotherapy only (GSE2603). In the TCGA dataset (n=503), a total of 98 patients showed TNBC, and 62 of them were chemotherapy patients.

For the meta analysis performed at last, 13 GEO datasets including metastasis-related event-free survival outcome and fixed effect (FE) models were used. To integrate gene expression data obtained from the multiple microarray platforms, the relative expression values of each dataset were calculated and integrated. That is, after calculating the relative expression value having the value of 0 to 1 for each gene in each TNBC data, several datasets were integrated according to the Entrez Gene ID. In all analyses of the present disclosure, when multiple probe sets exist for a particular gene, a probe set with the largest interquantile range (IQR) was chosen as a representative probe set. All analyzes were performed using the R statistical software and the Bioconductor package (http://www.R-project.org/ and http://bioconductor.org/).

To determine robust genetic indicators related to resistance to taxane in TNBC, three steps were applied. Three steps of finding genes related to taxane resistance (i.e., genetic indicators for first candidate genes) from 8 TNBC cell lines, extracting core genes (i.e., genetic indicators for second candidate genes) based on the GSEA, and then, finally selecting core genes related to prognosis (i.e., genetic indicators for third genes) were applied (see FIG. 1).

Figure 2A:
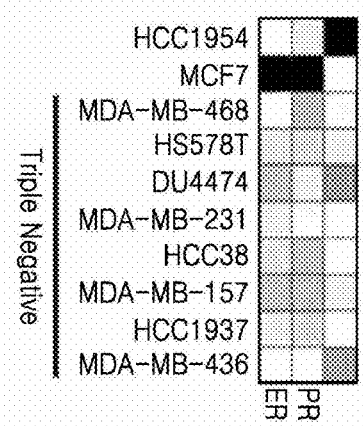
FIGS. 2A and 2B show the confirmation of triple-negative status of eight triple-negative TNBC cell lines and the discovery of first gene markers correlated with chemo-resistance to docetaxel.

Example 1. Identification of Biomarkers Related to Chemotherapy Susceptibility or Resistance in 8 TNBC Cell Lines The MCF7 cell line, which is ER positive and PR positive, was compared with the HCC1954 cell line, which is HER2 amplified, so as to confirm the triple-negative status of the 8 cell lines with low expression of ER, PR, and HER2 (see FIG. 2A). Table 2 shows the IC50 values and survival rates after docetaxel treatment at concentrations of 50 nM and 100 nM. To find genes that are positively or negatively correlated to taxane resistance among the eight types of the TNBC cell lines, the correlation coefficients between each gene and the rank sums of viability at docetaxel concentrations of 50 nM and 100 nM were calculated. When the following two conditions are satisfied, the genes are considered to have a significant correlation with resistance: gene expression range ($|\Delta Ex|$) is greater than 1, and the absolute value ($|r|$) of Pearson's or Spearman's correlation coefficient is greater than 0.5.

TABLE 2

Features of TNBC cell lines and resistance thereof to anticancer agent

| Cell line | Histology[a] | IC$_{50}$ (nM) | doctaxel (50 nM) Survival fraction | Rank | Docetaxel (100 nM) Survival fraction | Rank | Rank sum | Subtype[a] [9] | Mutations [9] |
|---|---|---|---|---|---|---|---|---|---|
| MDA-MB-468 | DC | 1.81 | 0.27 | 1 | 0.26 | 1 | 2 | BL1 | PTEN, RB1, SMAD4, TP53 |
| HS578T | CS | 11.08 | 0.32 | 2 | 0.29 | 3 | 5 | MSL | CDKN2A, MRAS, TP53 |

TABLE 2-continued

Features of TNBC cell lines and resistance thereof to anticancer agent

| Cell line | Histology[a] | IC$_{50}$ (nM) | doctaxel (50 nM) | | Docetaxel (100 nM) | | Rank sum | Subtype[a] [9] | Mutations [9] |
|---|---|---|---|---|---|---|---|---|---|
| | | | Survival fraction | Rank | Survival fraction | Rank | | | |
| DU4475 | DC | 11.57 | 0.37 | 3 | 0.27 | 2 | 5 | IM | APC, BRAF, MAP2K4, RB1 |
| MDA-MB-231 | IDC | 29.05 | 0.47 | 4 | 0.35 | 4 | 8 | MSL | BRAF, CDKN2A, KRAS, NF2, TP53, PDGFRA |
| HCC38 | DC | >100 | 0.57 | 5 | 0.53 | 5 | 10 | BL1 | CDKN2A, TP53 |
| MDA-MB-15T | MBC | >100 | 0.65 | 6 | 0.65 | 6 | 12 | MSL | NF1, TP53 |
| HCC1937 | DC | >100 | 0.76 | 7 | 0.70 | 7 | 14 | BL1 | BRCA1, TP53, MAPK13, MDC1 |
| MDA-MB-436 | IDC | >100 | 0.81 | 8 | 0.75 | 8 | 15 | MSL | BRCA1, TP53 |

Figure 2B:
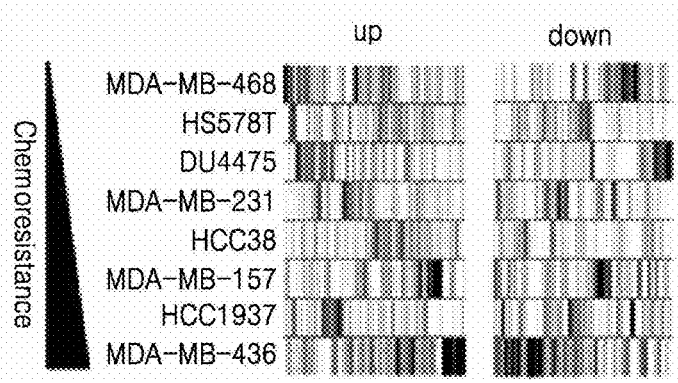

As a result, 2,113 positively correlated genes (i.e., gene markers for first positive/up candidate genes, r≥0.5) and 1,976 negatively correlated genes (i.e., gene markers for first negative/down candidate genes, r≤−0.5) were selected as final "gene markers for first candidate genes" associated with taxane resistance (see FIG. 2B).

Figure 3B:
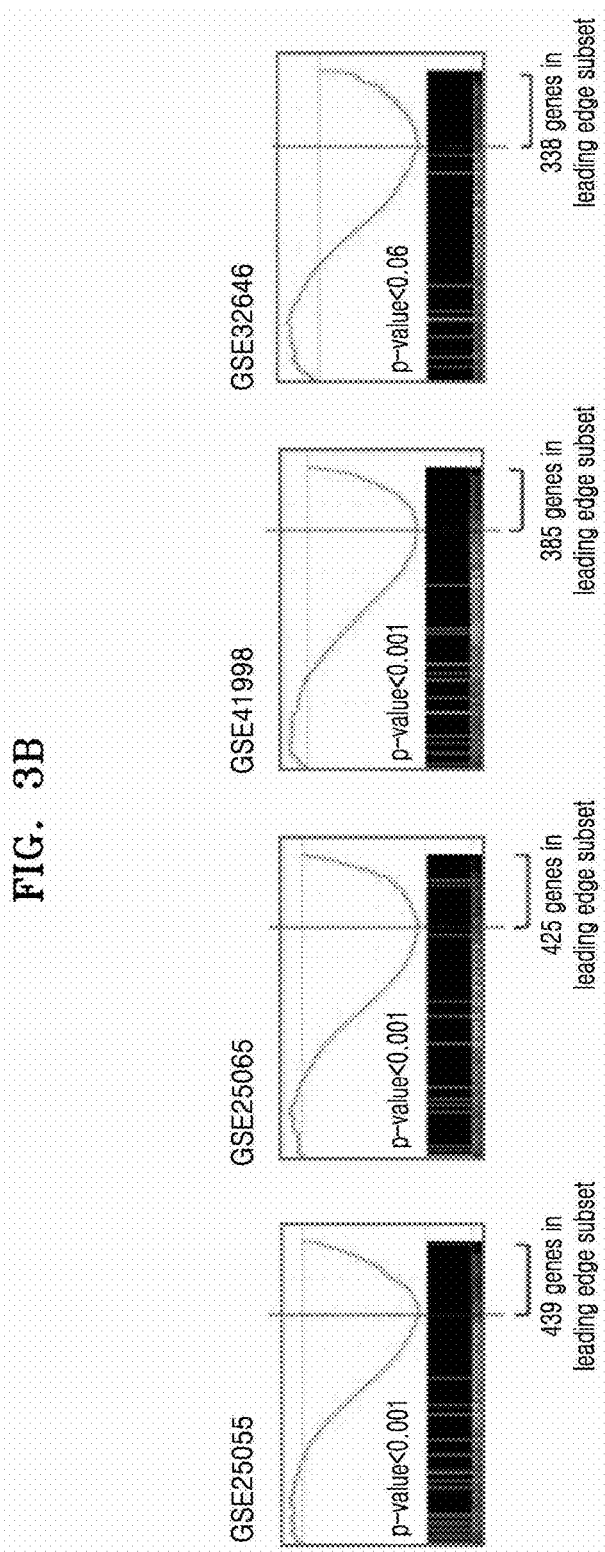
Figure 3C:
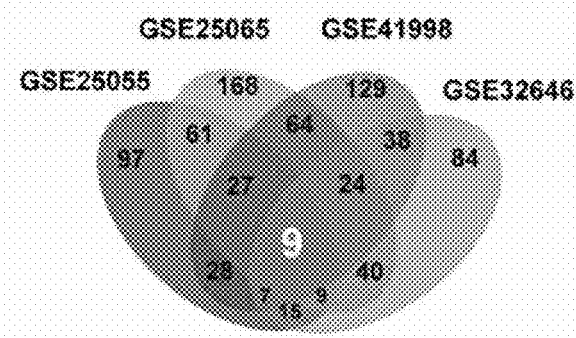
Figure 3D:
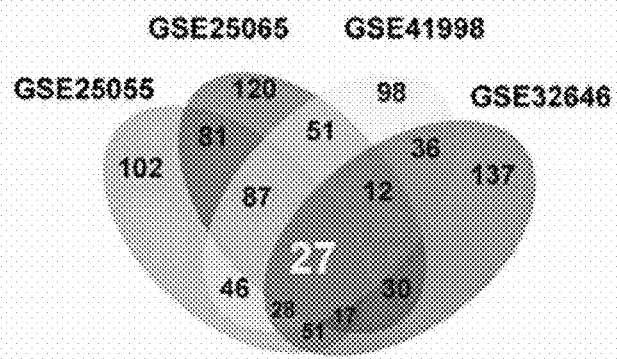

Example 2. Identification of Core Genes Associated with Prognosis Based on GSEA and Survival Analysis Using 4 Public TNBC Datasets To reduce the number of first candidate genes associated with taxane resistance found in Example 1, GSEA was applied using 4 TNBC datasets (i.e., designated exploratory datasets). That is, the GSEA analysis was performed using the first candidate genes as get sets in each exploratory dataset. Here, the preranking of the genes was ranked by differences (fold changes) in gene expression of the RD and pCR groups, and then, the GSEA method was applied. Referring to the GSEA analysis results, core genes belonging to the leading edge subset were obtained from each dataset (see FIGS. 3A and 3B), and 9 up- and 27 down-core genes commonly shown in the 4 data were selected as "second candidate genes" (see FIGS. 3C and 3D). In other words, the core genes commonly shown in the 4 exploratory datasets were defined as second candidate genes, and the core genes frequently found were defined as second gene markers (see FIGS. 3C and 3D). In the third step, based on the survival analysis method, such as nonparametric logrank test or parametric Cox regression analysis, only prognostic core genes that are statistically and significantly related to the survival outcomes (DRFS) were selected, thereby narrowing the scope of gene markers correlated with taxane resistance associated with response to the anticancer and prognosis prediction. That is, after performing the logrank tests at 3 cutoff points, and in one or more of these analyzes, 10 genes that were significantly correlated with DRFS were selected as 10 third prognostic core genes, also known as "third biomarkers". That is, as the third biomarkers by the logrank test, 3 up-core genes (CEBPD, MMP20, and WLS) and 7 down-core genes (ASF1A, ASPSCR1, CHAF1B, DNMT1, GINS2, GOLGA2P5, and SKA1), i.e., a total of 10 biomarkers regarding the response to the anticancer and prognosis prediction (Table 3).

Furthermore, in the case of the Cox regression analysis, 4 genes showing statistically significant correlation with DRFS (p-value<0.05) were selected as final "third 4 prognostic core biomarkers (or genes)". As the third genes by the Cox regression analysis, a total of 4 genes, i.e., 1 up-core gene (CEBPD) as the third gene, and 3 down-score genes ((ASPSCR1, CHAF1B, and SKA1), were defined as biomarkers for predicting response to the anticancer agent and prognosis (see Table 3).

TABLE 3

Biomarker derived according to 3-step processes according to the present disclosure

| | | 1st Step | | 2$^{nd}$ Step | | | | 3$^{rd}$ Step (GSE25066) | | | |
|---|---|---|---|---|---|---|---|---|---|---|---|
| | | | | Differential expression between RD vs pCR | | | | TNBC (n = 182) | | | |
| | | Correlation coefficient | | | | | | Log-rank test | | | |
| | | | | GSE 25055 | GSE 25065 | GSE 41998 | GSE 32646 | 0.25 quintile | | 0.5 quintile | |
| Class | Gene Symbol | Pearson | Spearman | (n = 119) log$_2$FC | (n = 63) log$_2$FC | (n = 64) log$_2$FC | (n = 25) log$_2$FC | Hazard ratio | p Value | Hazard ratio | p Value |
| Up | CEBPD | 0.79 | 0.93 | 0.28 | 0.67 | 0.25 | 0.25 | 1.57 | 0.18 | 1.15 | 0.59 |
| | MMP20 | 0.18 | 0.68 | 0.35 | 0.41 | 0.30 | 0.79 | 0.88 | 0.64 | 1.05 | 0.87 |
| | WLS | 0.44 | 0.55 | 0.31 | 0.93 | 0.35 | 0.48 | 1.13 | 0.69 | 1.13 | 0.63 |
| Down | ASF1A | −0.60 | −0.59 | −0.23 | −0.52 | −0.48 | −0.55 | 0.61 | 0.069 | 0.53 | 0.020 |
| | ASPSCR1 | −0.47 | −0.57 | −0.42 | −0.39 | −0.13 | −0.21 | 0.49 | 0.0086 | 0.68 | 0.15 |
| | CHAF1B | −0.77 | −0.74 | −1.07 | −1.36 | −0.27 | −0.25 | 0.48 | 0.0059 | 0.37 | 0.0005 |
| | DNMT1 | −0.88 | −0.90 | −0.16 | −0.24 | −0.21 | −0.33 | 0.90 | 0.71 | 0.84 | 0.50 |
| | GINS2 | −0.57 | −0.41 | −0.54 | −0.87 | −0.23 | −0.22 | 0.61 | 0.072 | 0.54 | 0.021 |
| | GOLGA2P5 | −0.57 | −0.50 | −0.22 | −0.45 | −0.14 | −0.28 | 0.80 | 0.45 | 0.81 | 0.41 |
| | SKA1 | −0.42 | −0.51 | −0.58 | −0.82 | −0.23 | −0.19 | 0.37 | 0.0002 | 0.57 | 0.034 |

TABLE 3-continued

| | | 3rd Step (GSE25066) | | | |
| | | TNBC (n = 182) | | | |
| | | Log-rank test | | | |
| | | 0.75 quintile | | Cox regression | |
| Class | Gene Symbol | Hazard ratio | p Value | Hazard ratio | p Value |
|---|---|---|---|---|---|
| Up | CEBPD | 1.86 | 0.022 | 1.39 | 0.029 |
| | MMP20 | 2.01 | 0.0097 | 1.13 | 0.13 |
| | WLS | 1.57 | 0.038 | 1.12 | 0.17 |
| Down | ASF1A | 0.72 | 0.32 | 0.83 | 0.17 |
| | ASPSCR1 | 0.66 | 0.20 | 0.77 | 0.0084 |
| | CHAF1B | 0.46 | 0.030 | 0.82 | 0.0019 |
| | DNMT1 | 0.44 | 0.023 | 0.73 | 0.11 |
| | GINS2 | 0.94 | 0.84 | 0.91 | 0.19 |
| | GOLGA2P5 | 0.46 | 0.031 | 0.89 | 0.26 |
| | SKA1 | 0.560 | 0.096 | 0.78 | 0.0046 |

Example 3. Verification of Response of Patients to Chemotherapy and Prognosis Using 10 Biomarkers To analyze the final 10 prognostic core genes from the combined datasets (4 exploratory datasets) of the 10 prognostic core genes defined by the Logrank test, "up score" and "down score" were calculated by averaging the relative expression levels of the up-score gene markers and the down-score gene markers based on the relative expression levels of 3 up-score genes (i.e., CEBPD, MMP20, and WLS) and 7 down-score genes (i.e., (ASF1A, ASPSCR1, CHAF1B, DNMT1, GINS2, GOLGA2P5, and SKA1) (see FIG. 4A).

The relative expression of the genes were calculated in the range of 0 to 1 in each TNBC patient in each exploratory dataset, and then, "up score" and "down score" in each patient by averaging the relative expression of the 3 up-score genes and the 7 down-score genes (see FIG. 4A). To analyze the determination of the response to the chemotherapy and the prognosis of the TNBC patients by these two values, scatter plots were made on the x- and y-axes of the two determined values, and divided into 2 groups by a diagonal line determined by "up score" and "down score" (see FIG. 4B left). Here, the slope of the diagonal line was determined by the ratio of which the "up score" range (value obtained by subtracting the minimum value from the maximum value) is the denominator and the "down score" range is the numerator. Also, the value of the intercept was determined by the value where the diagonal line passes through the median of the "up score" and the "down score".

As a result, it was found that the TNBC patients divided into 2 groups by levels of the diagonal line had statistical significance and showed different response to the anticancer agent-score genes (see FIG. 4B, left) and survival curve (FIG. 4B, right).

In this regard, for accurate prognosis measurement, the TNBC patients were divided into 3 groups and subjected to analysis of chemoresponse and survival, resulting in significant results (see FIG. 4C). That is, when divided into three groups by two diagonal lines having the same slope as the diagonal line in FIG. 4C (i.e., the patient groups were divided with the same the slope as FIG. 4B, but different y-intercept), so as to divide the upper, middle, and lower groups into 25%, 50%, and 25% of the total patient groups, the residual disease (RD) ratios belonging to the upper, middle, and lower groups were 37.3%, 65.6%, and 85.1%, respectively (see FIG. 4C, left). In addition, the TNBC patients belonging to each of the three groups showed distinct survival curves with statistical significance.

Example 4. Verification of Response of Patients to Chemotherapy and Prognosis Using 10 Biomarker According to the Present Disclosure in Independent Samples By using the data of 246 TNBC patients, including the metastasis-related event-free survival outcomes of 230 patients collected from the five public datasets (i.e., GSE16446, GSE19615, GSE20685, GSE22219, and GSE2603), the therapeutic chemoresponse and prognostic predictive ability of 10 biomarkers according to the present disclosure were analyzed in the independent TNBC dataset. Data associated with chemotherapy including taxane similar to the exploratory datasets may be also sued, but due to a lack of datasets, the datasets above were used for verification. As described in material and method above, considerably heterogeneous datasets were used for verification. Nevertheless, i.e., even though not all of the validation datasets were composed of highly heterogeneous (unknown) chemotherapy, which does not include taxene, and is not NAC, this combined independent dataset also demonstrated that the 10 core genes identified herein can predict prognosis very accurately. For the slope and intercepts of the diagonal line to be used in the verification, the same slope and intercepts of the diagonal line determined in the exploratory dataset analysis (see FIGS. 4B and 4C) were used. Even though the datasets have changed, i.e., even though the validated patients groups were divided according to the same criteria determined in the first exploratory dataset, the same results were obtained. These results indicate that clinically standardized criteria, i.e., predictive criteria that can be generally applied (the criteria for dividing the patient groups by prognosis) can be established. When dividing the validation dataset into two or three groups according to a method using the same slope and intercepts of the diagonal line as those defined in the exploratory dataset, the patients in each group showed different survival curves (see FIGS. 4D and 4E). When analyzed using the TCGA data which is another independent verification dataset, similar patterns were found in the TCGA dataset analysis consisting of 62 TNBC patients undergoing chemotherapy (see FIGS. 4F and 4G).

Example 5. Verification of Predicting Response to Chemotherapy and Prognosis of Patients Using Four Biomarkers Selected from 10 Biomarkers According to the Present Disclosure To analyze the predictive ability of the four prognostic core genes determined by the Cox regression analysis, "up score" and "down score" were calculated by averaging the degree of relative expression of each of the up-gene markers and the down-gene markers, based on the degree of relative expression of one up-core gene (i.e., CEBPD) and three down-core genes (i.e., ASPSCR1, CHAF1B, and SKA1) in the combined dataset (i.e., four exploratory datasets) (see FIG. 5A). The scatter plot was made with x- and x-axes for the "up score" and the "down score", respectively, and the patients were divided into two groups by a diagonal line determined by the "up score" and the "down score". Here, the slope of the diagonal line was determined by the ratio of which the "up score" range (value obtained by subtracting the minimum value from the maximum value) is the denominator and the "down score" range is the numerator. Also, the value of the intercept was determined by the value where the diagonal line passes through the median of the "up score" and the "down score".

Figure 5A:
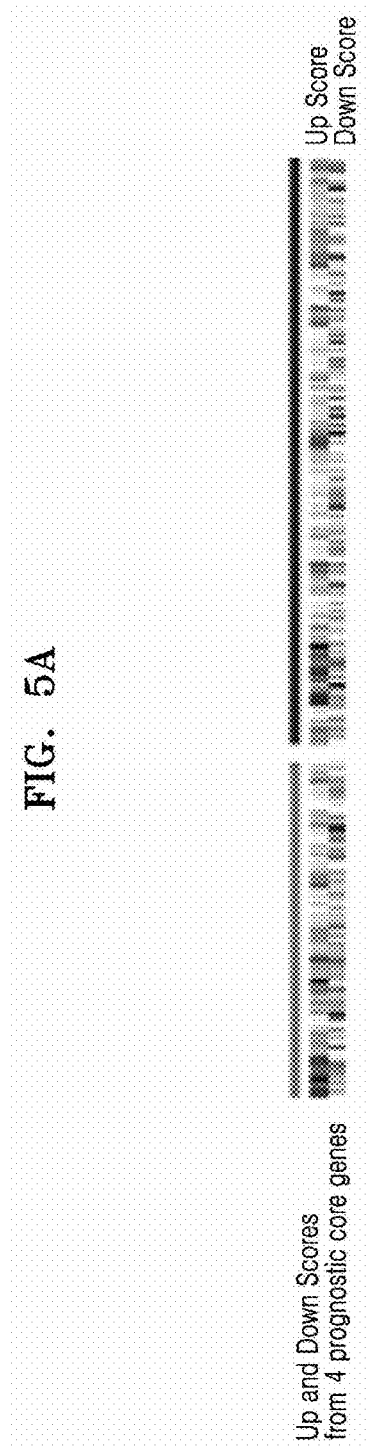
FIGS. 5A to 5G each show the result of verifying the prognostic predictive ability of four third gene markers (referred to as four prognostic core genes) selected from the second candidate genes by the Cox regression analysis.
Figure 5B:
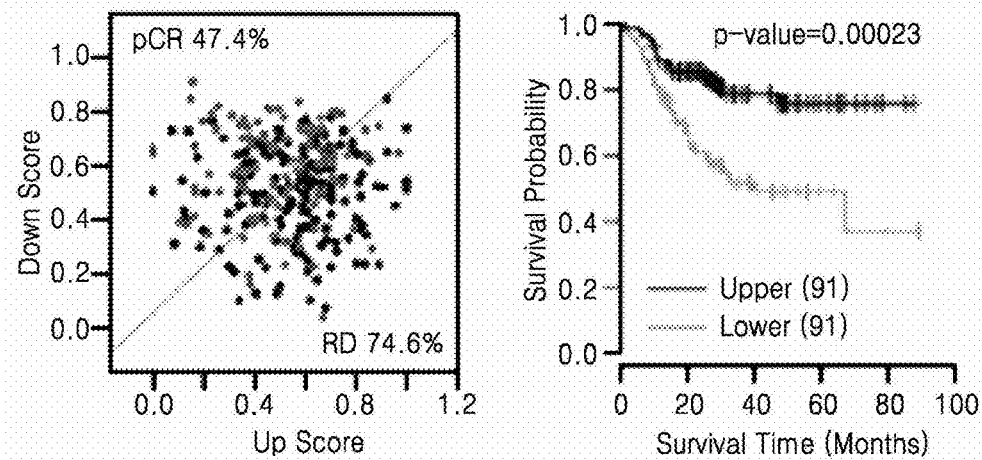

As a result, it was found that the TNBC patients divided into 2 groups by the diagonal line had statistical significance and showed different response to the anticancer agent (see FIG. 5B, left) and survival curve (FIG. 5B, right).

Figure 5C:
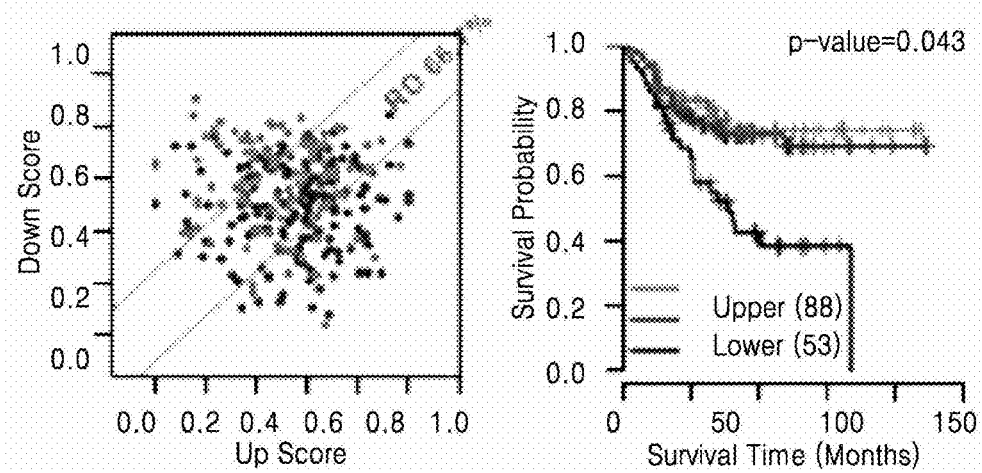
Figure 5D:
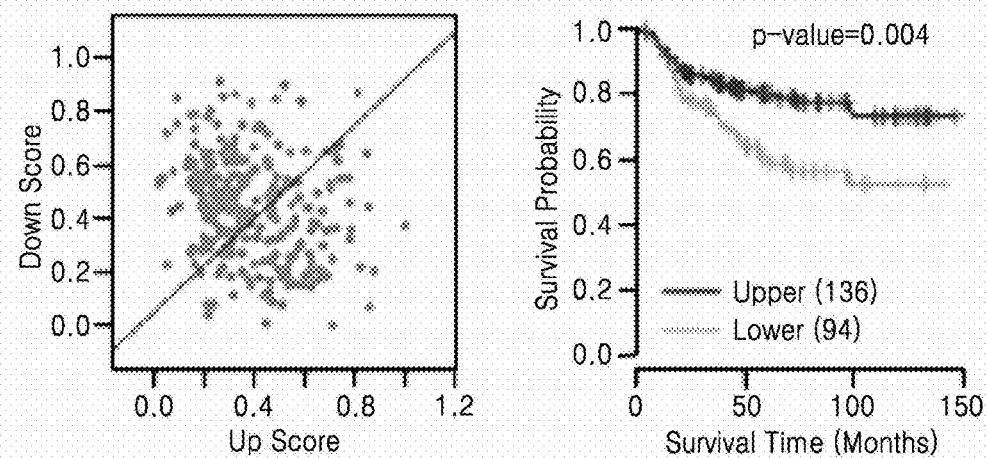
Figure 5E:
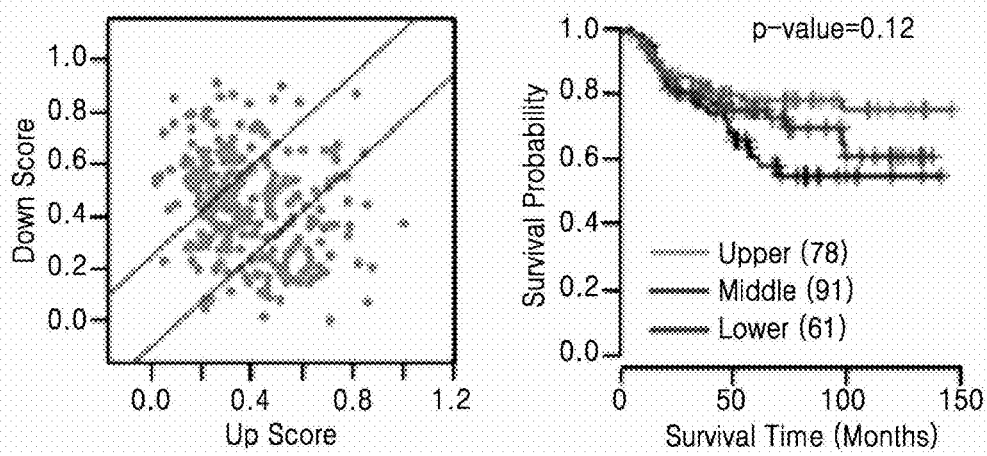
Figure 5F:
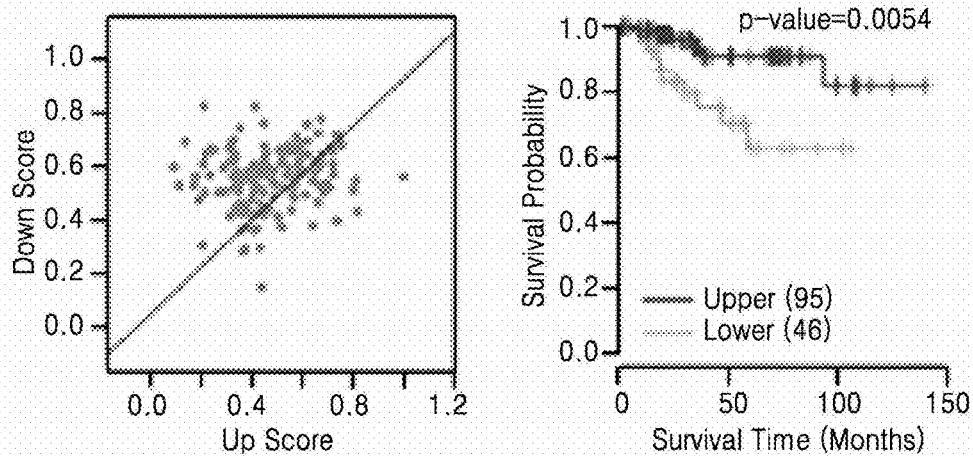
Figure 5G:
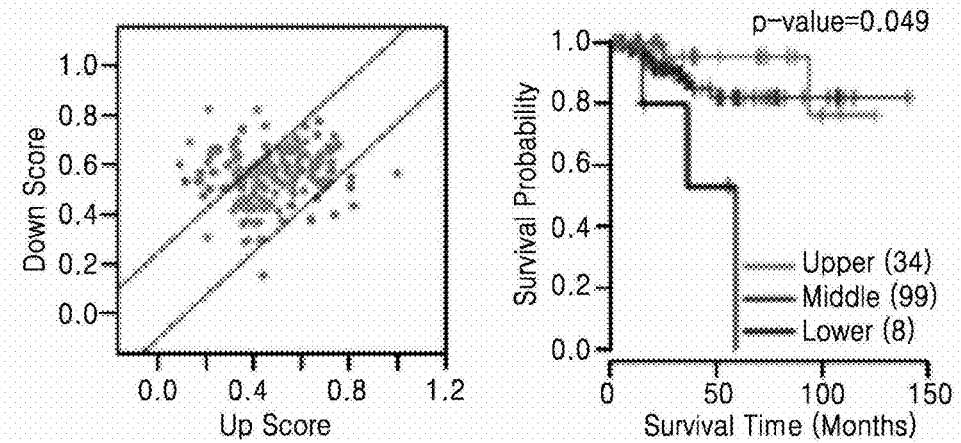

In this regard, for accurate prognosis measurement, the TNBC patients were divided into 3 groups and subjected to analysis of chemoresponse and survival, resulting in significant results (see FIG. 5C). That is, when divided into three groups by two diagonal lines having the same slope as the diagonal line in FIG. 4C (i.e., the patient groups were divided with the same the slope as FIG. 5B, but different y-intercept), so as to divide the upper, middle, and lower groups into 25%, 50%, and 25% of the total patient groups, the residual disease (RD) ratios belonging to the upper, middle, and lower groups were 37.3%, 65.6%, and 85.1%, respectively (see FIG. 5C, left). In addition, the TNBC patients belonging to each of the three groups showed different survival curves with statistical significance (see FIG. 5C, right).

Example 6. Verification of Response of to Chemotherapy and Prognosis of Patients Using 4 Biomarkers According to the Present Disclosure in Independent Samples By using the data of 246 TNBC patients, including the metastasis-related event-free survival outcomes of 230 patients collected from the five public datasets (i.e., GSE16446, GSE19615, GSE20685, GSE22219, and GSE2603), the therapeutic chemoresponse and prognostic predictive ability of four third prognostic core genes were analyzed in the independent TNBC dataset. For the slope and intercepts of the diagonal line to be used in the verification, the same slope and intercepts of the diagonal line determined in the exploratory dataset analysis (see FIGS. 5B and 5C) were used. As a result, the patients in each group showed different survival curves (see FIGS. 5D and 5E). When analyzed using the TCGA data which is another independent verification dataset, similar patterns were found in the TCGA dataset analysis consisting of 141 TNBC patients undergoing chemotherapy (see FIGS. 5F and 5G).

Example 7. Analysis of Age at Diagnosis and Stage of 10 and 4 Biomarkers According to the Present Disclosure and Independent Prognostic Prediction Biomarkers To verify whether the final 10 and 4 core genes were independent prognostic factors that can independently predict prognosis from the age at diagnosis and stage at the time of diagnosis in patients previously known to be associated with prognosis of breast cancer, the multivariable Cox regression analysis was performed with two datasets of GSE25066 and TCGA.

As a result, it was confirmed that, even after the age at diagnosis and the stage at the time of the diagnosis of the patients were modified, 10 and 4 biomarkers were able to predict the prognosis statistically significantly.

TABLE 4

Results of multivariable survival analysis

| Prognostic core genes | Dataset | Covariates | Hazard ratio (95% CI) | p-value | Likelihood Ratio Test |
|---|---|---|---|---|---|
| 10 prognostic core genes | GSE25066 (Exploratory) (n = 175) | Age (≥40 vs <40) | 1.02 (0.53, 1.97) | 0.96 | $4.5 \times 10^{-3}$ |
| | | Stage (III vs II) | 3.08 (1.73, 5.49) | 0.00013 | |
| | | 10 prognostic core genes (Upper vs Lower) | 0.43 (0.24, 0.77) | 0.0041 | |
| | TCGA (Validation) (n = 139) | Age (≥40 vs <40) | 0.24 (0.06, 0.94) | 0.04 | $1.1 \times 10^{-7}$ |
| | | Stage (III/IV vs I/II) | 23.5 (7.48, 73.8) | $6.4 \times 10^{-2}$ | |
| | | 10 prognostic core genes (Upper vs Lower) | 0.29 (0.10, 0.83) | 0.021 | |
| 4 prognostic core genes | GSE25066 (Exploratory) (n = 175) | Age (≥40 vs <40) | 1.05 (0.54, 2.04) | 0.88 | $4.7 \times 10^{-3}$ |
| | | Stage (III vs II) | 2.56 (1.44, 4.56) | 0.0014 | |
| | | 4 prognostic core genes (Upper vs Lower) | 0.43 (0.25, 0.77) | 0.0040 | |
| | TCGA (Validation) (n = 139) | Age (≥40 vs <40) | 0.40 (0.10, 1.50) | 0.17 | $5.0 \times 10^{-4}$ |
| | | Stage (III/IV vs I/II) | 20.4 (6.93, 60.2) | $4.5 \times 10^{-4}$ | |
| | | 4 prognostic core genes (Upper vs Lower) | 0.24 (0.08, 0.71) | 0.0099 | |

In the GSE25066 dataset, in the case of survival analysis by logrank test by dividing the patient groups with 4 core genes after stratificating the age at diagnosis and the stage at the time of diagnosis of the patients, statistical significance was obtained at the age of 40 years and older, and different survival curves were shown (see FIG. 6A). In the GSE25066 dataset, statistical significance was not obtained at the age under 40 years. However, in the case of patients with low stages and classified into the upper group by four core genes, very good prognosis was shown (see FIG. 6B). In the TOGA dataset, in the case of survival analysis by logrank test by dividing the patient groups with 4 core genes after stratificating the age at diagnosis and the stage at the time of diagnosis of the patients, statistical significance was obtained at the age of 40 years and older and under 40 years, and different survival curves were shown (see FIGS. 6C and 6D).

Hereinabove, although exemplary embodiments of the present disclosure have been described in detail. However, the scope of the present disclosure is not limited thereto, and belongs to various modifications and improvements of those skilled in the art using the basic concepts of the present disclosure defined in the following claims.

All the technical terms used in the present disclosure, unless defined otherwise, are used in the meaning as commonly understood by those skilled in the art in the related field of the present disclosure. The contents of all publications described herein by reference documents are incorporated into the present disclosure.

The invention claimed is:

1. A method of treating a patient with triple-negative breast cancer, the method comprising:
   providing a biological sample derived from a target subject in need of the treatment for triple negative breast cancer, wherein the biological sample comprises breast tissue or a circulating cancer cell;
   measuring an expression level of one or more biomarkers selected from a first group and three or more biomarkers selected from a second group, at a nucleic acid level or a protein level, from the biological sample, wherein the biomarkers of the first group consist of CCAAT/enhancer-binding protein delta (CEBPD), matrix metalloproteinase-20 (MMP20), and wntless Wnt ligand secretion mediator (WLS), and the biomarkers of the second group consist of anti-silencing function 1A histone chaperone (ASF1A), ALVEOLAR SOFT PART SARCOMA CHROMOSOME REGION (ASP-SCR1), chromatin assembly factor 1subunit B (CHAF1B), DNA methyltransferase 1 (DNMT1), GINS complex subunit 2 (GINS2), golgin subfamily A member 2B (GOLGA2P5), and spindle and kinetochore-associated protein 1 (SKA1), wherein the measuring includes measuring at CEBPD from the first group and ASPSCR1, CHAF1B, and SKA1 from the second group; and
   associating the target subject with chemoresponse and prognosis by comparing the results of the measuring with those of a reference group, and identifying the patient as having poor prognosis, wherein the one or more biomarkers of the first group are up score genes showing resistance to chemotherapeutic agents with increased expression in a patient with poor prognosis, and the three or more biomarkers of the second group are down score genes showing resistance to the chemotherapeutic agents with reduced expression in a patient with poor prognosis; and
   administering an effective amount of chemotherapeutic agents to the patient with poor prognosis.

2. The method of claim 1,
   wherein, in the associating,
   the reference group refers to a group of patients with triple-negative breast cancer, and provides an expression level determined for each biomarker in a sample derived from a patient having information on response to the anticancer agents and/or prognosis, and
   when, compared to the median or mean value of the reference group, an expression level of the one or more biomarkers of the first group increases and an expression level of the three or more biomarkers of the second group decreases, the target subject is determined to have poor prognosis, and when, compared to the median or mean value of the reference group, an expression level of the one or more biomarkers of the first group decreases and an expression level of the three or more biomarkers of the second group increases, the target subject is determined to have good prognosis.

3. The method of claim 1,
   wherein the measuring further comprises the steps of:
   determining a relative expression level of each of the one or more biomarkers of the first group and the three or more biomarkers of the second group, based on the measured expression level; calculating an up score by averaging the relative expression level of the one or more biomarkers of the first group; and calculating a down score by averaging the relative expression level of the three or more biomarkers of the second group,
   in the associating,
   the results of the reference group are shown in a scatter plot with x- and y-axes for the up score of the one or more biomarkers of the first group and the down score of the three or more biomarkers of the second group, respectively, wherein the up score and the down score are determined from the patients with triple-negative breast cancer and having information on response to the anticancer agents, and the scatter plot includes a first diagonal line passing through a point with x- and y-values for the median value of the up score and the median value of the down score, respectively, and having a slope determined by a denominator and a numerator, wherein the denominator is obtained by subtracting a minimum value of the up score from a maximum value of the up score, and the numerator is obtained by subtracting a minimum value of the down score from a maximum value of the down score, and
   in the associating,
   when the up score and the down score determined from the target subject are plotted in the scatter plot, and the point belongs to a region above the first diagonal line, the target subject is determined to have good response to the anticancer agents and good prognosis, and when the point belongs to a region below the first diagonal line, the target subject is determined to have poor response to the anticancer agents and poor prognosis.

4. The method of claim 1, wherein the chemotherapeutic agent comprises a taxane-based anticancer agent, docetaxel, paclitaxel, or cabazitaxel, a vinca alkaloid chemotherapeutic agent, vincristine, vinblastine, anthracycline, 5-fluorouracil, or cyclophosphamide.

* * * * *